(12) United States Patent
Lau et al.

(10) Patent No.: US 11,771,139 B2
(45) Date of Patent: *Oct. 3, 2023

(54) NON-NICOTINE ELECTRONIC VAPING DEVICE WITH MEMORY MODULE

(71) Applicant: Altria Client Services LLC, Richmond, VA (US)

(72) Inventors: Raymond W. Lau, Richmond, VA (US); Eric Hawes, Richmond, VA (US); Loi Ying Liu, Hong Kong (CN)

(73) Assignee: ALTRIA CLIENT SERVICES LLC, Richmond, VA (US)

( * ) Notice: Subject to any disclaimer, the term of this patent is extended or adjusted under 35 U.S.C. 154(b) by 713 days.

This patent is subject to a terminal disclaimer.

(21) Appl. No.: 16/741,227

(22) Filed: Jan. 13, 2020

(65) Prior Publication Data

US 2021/0212381 A1 Jul. 15, 2021

(51) Int. Cl.
*A24F 40/57* (2020.01)
*A24F 40/42* (2020.01)
(Continued)

(52) U.S. Cl.
CPC ............ *A24F 40/57* (2020.01); *A24B 15/167* (2016.11); *A24F 40/42* (2020.01); *A24F 40/46* (2020.01);
(Continued)

(58) Field of Classification Search
CPC .......... A24F 40/42; A24F 40/46; A24F 40/57; G11C 17/16; G11C 17/18
See application file for complete search history.

(56) References Cited

U.S. PATENT DOCUMENTS

| 5,301,143 A | 4/1994 | Ohri et al. |
|---|---|---|
| 6,803,545 B2 | 10/2004 | Blake et al. |

(Continued)

FOREIGN PATENT DOCUMENTS

| CN | 101375345 A | * | 2/2009 | ............ G11C 17/18 |
|---|---|---|---|---|
| CN | 203137026 | | 8/2013 | |

(Continued)

OTHER PUBLICATIONS

International Preliminary Report on Patentability for International Application No. PCT/EP2021/050592 dated Jul. 28, 2022.
(Continued)

*Primary Examiner* — Hae Moon Hyeon
(74) *Attorney, Agent, or Firm* — Harness, Dickey & Pierce, P.L.C.

(57) ABSTRACT

A non-nicotine e-vaping device includes a heater, a power control circuit, and a memory module. The heater element is configured to heat a non-nicotine pre-vapor formulation, the non-nicotine pre-vapor formulation being devoid of nicotine and including at least one non-nicotine compound. The power control circuit is coupled to the heater element through a wire. The power control circuit is configured to apply a pulse width modulated power signal to the heater element through the wire, and to receive information over the wire. The memory module is configured to detect a plurality of pulses in the pulse width modulated power signal, record information based on the detected plurality of pulses, and output the recorded information to the power control circuit via the wire.

14 Claims, 12 Drawing Sheets

(51) Int. Cl.
  *A24B 15/167* (2020.01)
  *A24F 40/46* (2020.01)
  *A24F 40/51* (2020.01)
  *G11C 17/16* (2006.01)
  *G11C 17/18* (2006.01)
  *H05B 1/02* (2006.01)

(52) U.S. Cl.
  CPC .............. *A24F 40/51* (2020.01); *G11C 17/16* (2013.01); *G11C 17/18* (2013.01); *H05B 1/0297* (2013.01)

(56) References Cited

U.S. PATENT DOCUMENTS

| | | | |
|---|---|---|---|
| 9,980,514 B2* | 5/2018 | Malamud | H05B 1/0244 |
| 10,143,232 B2* | 12/2018 | Talon | A24F 40/50 |
| 2007/0042515 A1 | 2/2007 | Edelen | |
| 2007/0086644 A1 | 4/2007 | Wilson et al. | |
| 2011/0265806 A1* | 11/2011 | Alarcon | A24F 47/00 131/273 |
| 2014/0338685 A1 | 11/2014 | Amir | |
| 2016/0316821 A1 | 11/2016 | Liu | |
| 2017/0027229 A1 | 2/2017 | Cameron | |
| 2017/0135412 A1 | 5/2017 | Cameron | |
| 2017/0215485 A1 | 8/2017 | Zitzke | |
| 2017/0231276 A1 | 8/2017 | Mironov et al. | |
| 2018/0020729 A1 | 1/2018 | Alarcon et al. | |
| 2018/0021328 A1 | 1/2018 | Myers et al. | |
| 2018/0104214 A1 | 4/2018 | Raichman | |
| 2018/0132530 A1 | 5/2018 | Rogers et al. | |
| 2018/0263283 A1* | 9/2018 | Popplewell | G05B 13/024 |
| 2019/0239566 A1* | 8/2019 | Alarcon | H05B 1/0252 |
| 2021/0153565 A1* | 5/2021 | Twite | A24F 40/42 |
| 2021/0212380 A1* | 7/2021 | Lau | A24F 40/46 |
| 2021/0401061 A1* | 12/2021 | Davis | A24F 40/57 |

FOREIGN PATENT DOCUMENTS

| | | | |
|---|---|---|---|
| EP | 2856893 A1 | 4/2015 | |
| EP | 3098738 A1 | 11/2016 | |
| WO | WO-2014-066730 A1 | 5/2014 | |
| WO | WO-2017-153467 A1 | 9/2017 | |
| WO | WO-2017153467 A1 * | 9/2017 | .......... A24B 15/167 |
| WO | WO-2019173923 A1 | 9/2019 | |

OTHER PUBLICATIONS

International Search Report and Written Opinion of the International Searching Authority for corresponding International Application No. PCT/EP2021/050592 dated Mar. 26, 2021.
Charles H. Small, "User-programmable gate arrays," EDN, 34. pp. 146-155, published Apr. 27, 1989.
Clive Maxfield, "Field-programmable devices," EDN, 41, pp. 201-206, Oct. 10, 1996.
Rachel Z. Behar et al., "Puffing Topography and Nicotine Intake of Electronic Cigarette Users," PLoS ONE doi:10.1371/journal.pone. 0117222, pp. 1-18, Feb. 9, 2015.
UK Vapour Brands Limited, "TECC arc4 User Manual," Mar. 11, 2016.
International Preliminary Report on Patentability for corresponding International Application No. PCT/US2021/012891 dated Jul. 28, 2022.
International Search Report and Written Opinion of the International Searching Authority for corresponding International Application No. PCT/US2021/012891 dated May 4, 2021.
U.S. Office Action for co-pending U.S. Appl. No. 16/741,109 dated Jul. 20, 2022.
U.S. Notice of Allowance for co-pending U.S. Appl. No. 16/741,109 dated Nov. 21, 2022.
U.S. Notice of Allowance for co-pending U.S. Appl. No. 16/741,109 dated Jan. 26, 2023.

* cited by examiner

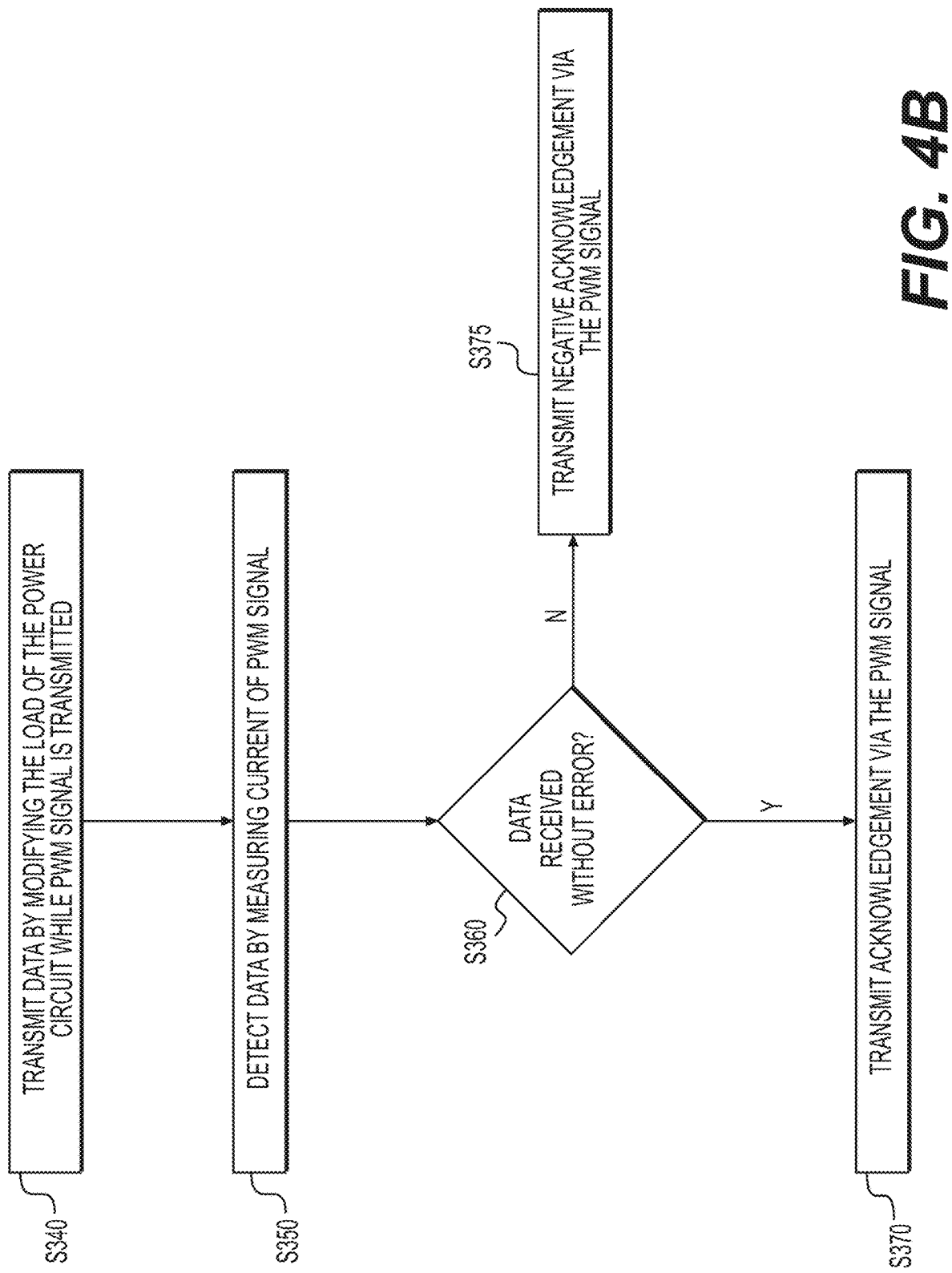

NON-NICOTINE ELECTRONIC VAPING DEVICE WITH MEMORY MODULE

BACKGROUND

Field

The present disclosure relates to a non-nicotine electronic vaping or non-nicotine e-vaping device.

Description of Related Art

A non-nicotine electronic vaping or non-nicotine e-vaping device includes a heating element that heats a non-nicotine pre-vapor formulation to produce a non-nicotine vapor.

A non-nicotine e-vaping device includes a power supply, such as a rechargeable battery, arranged in the device. The power supply is electrically connected to the heater. The power supply provides power to the heater such that the heater heats to a temperature sufficient to convert the non-nicotine pre-vapor formulation to a non-nicotine vapor. The non-nicotine vapor exits the non-nicotine e-vaping device through a mouthpiece including at least one outlet. Non-nicotine e-vaping devices may include a memory, such as heat resistant Electrically Erasable Programmable Read-Only Memory (EEPROM).

SUMMARY

At least one example embodiment provides a non-nicotine e-vaping device including: a heater element configured to heat a non-nicotine pre-vapor formulation, the non-nicotine pre-vapor formulation being devoid of nicotine and including at least one non-nicotine compound; a power control circuit coupled to the heater element through a wire, the power control circuit configured to apply a pulse width modulated power signal to the heater element through the wire, and receive information over the wire; and a memory module configured. The memory module is configured to: detect a plurality of pulses in the pulse width modulated power signal; record information based on the detected plurality of pulses; and output the recorded information to the power control circuit via the wire.

At least one other example embodiment provides a non-nicotine cartridge of a non-nicotine e-vaping device, the non-nicotine cartridge including: an array of fuses, each fuse in the array of fuses configured to open based on a threshold voltage; a memory controller configured to receive a pulse width modulated power signal via a wire, and apply a voltage greater than or equal to the threshold voltage across one or more fuses in the array of fuses based on a plurality of pulses in the pulse width modulated power signal; a reservoir configured to hold a non-nicotine pre-vapor formulation, the non-nicotine pre-vapor formulation being devoid of nicotine and including at least one non-nicotine compound; and a heater element configured to heat non-nicotine pre-vapor formulation drawn from the reservoir. The heater element is part of the wire.

At least one other example embodiment provides a non-nicotine cartridge of a non-nicotine e-vaping device. The non-nicotine cartridge includes: a memory; a memory controller coupled to the memory, wherein the memory controller is configured to read information stored in the memory, and output the information over a wire by modifying a pulse width modulated power signal carried by the wire; a reservoir configured to hold a non-nicotine pre-vapor formulation, the non-nicotine pre-vapor formulation being devoid of nicotine and including at least one non-nicotine compound; and a heater element configured to heat non-nicotine pre-vapor formulation drawn from the reservoir. The heater element is part of the wire.

At least one other example embodiment provides a non-nicotine e-vaping device including: a reservoir configured to hold a non-nicotine pre-vapor formulation, the non-nicotine pre-vapor formulation being devoid of nicotine and including at least one non-nicotine compound; a heater element configured to heat non-nicotine pre-vapor formulation drawn from the reservoir; a power application circuit configured to output a pulse width modulated power signal to the heater element via a wire, the heater element being part of the wire; and an integrated circuit including an analog to digital converter (ADC). The ADC is configured to receive a data transmission via the wire by detecting a change in current in one or more pulses of the pulse width modulated power signal, and control the power application circuit to output the pulse width modulated power signal.

At least one other example embodiment provides a memory module for a non-nicotine cartridge of a non-nicotine e-vaping device, the memory module comprising: an array of fuses, each fuse in the array of fuses configured to open based on a threshold voltage; a memory controller configured to receive a pulse width modulated power signal via a wire, and apply a voltage greater than or equal to the threshold voltage across one or more fuses in the array of fuses based on a plurality of pulses in the pulse width modulated power signal.

At least one other example embodiment provides a memory module for a non-nicotine cartridge of a non-nicotine e-vaping device, the memory module comprising: a memory; and a memory controller coupled to the memory, the memory controller configured to read information stored in the memory, and output the information over a wire by modifying a pulse width modulated power signal carried by the wire.

At least one other example embodiment provides a power control circuit for a non-nicotine e-vaping device, the power control circuit comprising: a power application circuit configured to output a pulse width modulated power signal to a heater element via a wire; and an integrated circuit including an analog to digital converter (ADC) configured to receive a data transmission via the wire by detecting a change in current in one or more pulses of the pulse width modulated power signal, and control the power application circuit to output the pulse width modulated power signal, wherein the heater element is part of the wire.

BRIEF DESCRIPTION OF THE DRAWINGS

Non-limiting example embodiments described herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

FIG. 4B is a flow diagram illustrating a method for transmitting information to the main body according to at least one example embodiment.

DETAILED DESCRIPTION

Figure 1:
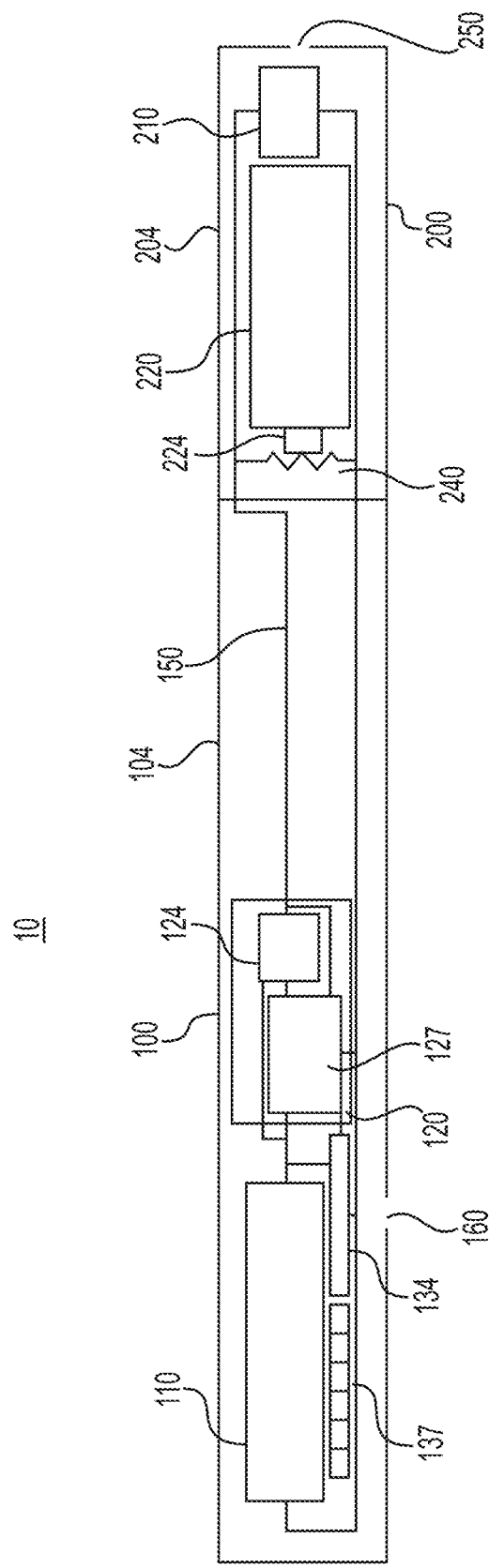
FIG. 1 is a simplified view of a non-nicotine electronic vaping or non-nicotine e-vaping device according to at least one example embodiment.

Some detailed example embodiments are disclosed herein. However, specific structural and functional details disclosed herein are merely representative for purposes of describing example embodiments. Example embodiments may, however, be embodied in many alternate forms and should not be construed as limited to only the example embodiments set forth herein.

Accordingly, while example embodiments are capable of various modifications and alternative forms, example embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives falling within the scope of example embodiments. Like numbers refer to like elements throughout the description of the figures.

FIG. 1 is a simplified view of a non-nicotine e-vaping device 10 according to at least one example embodiment.

Referring to FIG. 1, in at least one example embodiment, a non-nicotine electronic vaping device (non-nicotine e-vaping device) 10 includes a main body (or first section) 100 and a replaceable cartridge (or second section) 200. The first section 100 and the second section 200 may be coupled together. For example, the first section 100 and the second section 200 may be coupled together using connectors (not shown). The connectors may include a male connector piece with reciprocal threads on the first section 100 and a female connector piece including reciprocal threads on the second section 200. The female and male connectors may connect by rotating the threads together. Alternatively, the connectors may be snug-fit connectors, detent connectors, clamp connectors, clasp connectors, or the like. Moreover, the positioning of the male and female connectors may be reversed as desired such that the female connector piece is part of the first section 100, and the male connector piece is part of the second section 200.

In the example embodiment shown in FIG. 1, the first section 100 includes a power supply 110, a power control circuit 120, a sensor 134, and an LED array 137. The power control circuit 120 includes a power circuit (or power application circuit) 124 and an integrated circuit 127.

The second section 200 includes a memory module 210, a reservoir 220 and a heater 240 (or heater element). The reservoir 220 is configured to hold a non-nicotine pre-vapor formulation. The power control circuit 120 and the memory module 210 may be electrically connected through the power wire 150. As will be described in further detail below, the power control circuit 120 and the memory module 210 may communicate information over the power wire 150. The power control circuit 120 may also provide power to the heater 240 and the memory module 210 over the power wire 150.

The power wire 150 may be a single wire or multiple wires. The heater 240 may be part of the power wire 150. The power wire 150 may also include connecting elements or other conductive elements.

In some example embodiments, one or both of the sensor 134 and air inlet 160 may be included in the second section 200. The first section 100 may include a first outer housing 104. The second section 200 may include a second outer housing 204.

The integrated circuit 127 may control the power circuit 124, the sensor 134 and the LED array 137. The integrated circuit 127 may also receive a sensor signal from the sensor 134. The integrated circuit 127 may control the power circuit 124 to provide a pulse width modulated (PWM) signal (or PWM power signal) to the heater 240 and the memory module 210 over the power wire 150.

The integrated circuit 127 may also receive information from the memory module 210 over the power wire 150. The information received from the memory module 210 may indicate, for example, a level of non-nicotine pre-vapor formulation in the reservoir 220. The integrated circuit 127 may control the LED array 137 to display the level of non-nicotine pre-vapor formation based on the received information. For example, the LED array 137 may include 6 LEDs. In this example, if the information received from the memory module 210 indicates that the reservoir 220 is half full, then the integrated circuit 127 may control the LED array 137 to light 3 of the 6 LEDs to show that the reservoir 220 is half full.

The sensor 134 may be a capacitive sensor capable of sensing an internal pressure drop within the first section 100. In at least one example embodiment, the sensor 134 is configured to generate an output indicative of a magnitude and direction of airflow through the non-nicotine e-vaping device 10. In this example, the integrated circuit 127 receives an output of the sensor 134, and determines if (1) the direction of the airflow indicates an application of negative pressure to (e.g., draw on) the air outlet 250 (versus positive pressure or blowing) and (2) the magnitude of the application of negative pressure exceeds a threshold level. The threshold level may be set based on empirical data. If these non-nicotine vaping conditions are met, then the integrated circuit 127 controls the power circuit 124 to output a PWM signal to the heater 240 via the power wire 150.

According to at least one example embodiment, the sensor 134 is discussed with respect to a capacitive sensor. However, sensor 134 may be any suitable pressure sensor, for example, a microelectromechanical system (MEMS) including a piezo-resistive or other pressure sensor.

The heater 240 may heat non-nicotine pre-vapor formulation drawn from the reservoir 220 by a wick 224. The wick 224 may draw the non-nicotine pre-vapor formulation from the reservoir 220 (e.g., via capillary action), and the heater 240 may heat the non-nicotine pre-vapor formulation in the central portion of the wick 224 to a temperature sufficient to vaporize the non-nicotine pre-vapor formulation thereby generating a non-nicotine vapor. As referred to herein, a non-nicotine vapor is any matter generated or outputted from any non-nicotine e-vaping device 10 according to any of the example embodiments disclosed herein. The airflow may carry the non-nicotine vapor out the air outlet 250.

In still other example embodiments, the air inlet 160 may be between the first section 100 and the second section 200. In some example embodiments the heater 240 may be in the first section 100.

In at least one example embodiment, the reservoir 220 may include a storage medium and the storage medium may be a fibrous material including at least one of cotton (e.g., a winding of cotton gauze), polyethylene, polyester, rayon, combinations thereof, or the like. In at least one other example embodiment, the reservoir 220 may include a filled tank lacking any storage medium and containing only non-nicotine pre-vapor formulation. The reservoir 220 may be sized and configured to hold enough non-nicotine pre-vapor formulation such that the non-nicotine e-vaping device 10 may be configured for non-nicotine vaping for at least about 1000 seconds. Moreover, the non-nicotine e-vaping device 10 (more specifically the integrated circuit 127) may be configured to allow each puff to last a maximum of about 5 seconds.

In at least one example embodiment, the non-nicotine pre-vapor formulation is a material or combination of materials that may be transformed into a non-nicotine vapor.

In at least one example embodiment, a flavoring (at least one flavorant) and/or a non-nicotine compound may be included in the non-nicotine pre-vapor formulation. In at least one example embodiment, the non-nicotine pre-vapor formulation is a liquid, solid, dispersion and/or a gel formulation including, but not limited to, water, beads, solvents, active ingredients, ethanol, plant extracts, natural or artificial flavors, and/or at least one non-nicotine vapor former such as glycerin and propylene glycol.

The non-nicotine compound is devoid of nicotine. In at least one example embodiment, the non-nicotine compound does not include tobacco, nor is the compound derived from tobacco. In at least one example embodiment, the non-nicotine compound is *cannabis*, or includes at least one *cannabis*-derived constituent. In at least one example embodiment, a *cannabis*-derived constituent includes at least one of a *cannabis*-derived cannabinoid (e.g., a phytocannabinoid, or a cannabinoid synthesized by a *cannabis* plant), at least one *cannabis*-derive terpene, at least one *cannabis*-derived flavonoid, or combinations thereof.

In at least one example embodiment, the non-nicotine compound is in the form of, or included in, a solid, a semi-solid, a gel, a hydrogel, or combinations thereof, and the non-nicotine compound is infused into, or co-mingled or combined within, the non-nicotine pre-vapor formulation. In at least one example embodiment, the non-nicotine compound is in the form of, or included in, a liquid or a partial-liquid, that includes an extract, an oil, a tincture, a suspension, a dispersion, a colloid, an alcohol, a general non-neutral (slightly acidic or slightly basic) solution, or combinations thereof, and the non-nicotine compound is infused into, or comingled or combined within, the non-nicotine pre-vapor formulation. In at least one example embodiment, the non-nicotine compound is a constituent of the non-nicotine pre-vapor formulation. In at least one example embodiment, the non-nicotine pre-vapor formulation is, or is part of, a dispersion, a suspension, a gel, a hydrogel, a colloid, or combinations thereof, and the non-nicotine compound is a constituent of the non-nicotine pre-vapor formulation.

In at least one example embodiment, the non-nicotine compound undergoes a slow, natural decarboxylation process over an extended duration of time at low temperatures, including at or below room temperature (72° F.). In at least one example embodiment, the non-nicotine compound may undergo a significantly elevated decarboxylation process, on the order of 50% decarboxylation or greater if the non-nicotine compound is exposed to elevated temperatures especially in the range of about 175° F. or greater over a period of time (minutes or hours, at a relatively low pressure such as 1 atmosphere), where even further elevated temperatures (about 240° F. or greater) can cause a rapid or instantaneous decarboxylation to occur at a potentially high decarboxylation rate (50% or more), though ever further elevated temperatures can cause a degradation of some or all of the chemical properties of the non-nicotine compounds.

In at least one example embodiment, the at least one non-nicotine vapor former of the non-nicotine pre-vapor formulation includes diols (such as propylene glycol and/or 1,3-propanediol), glycerin and combinations, or sub-combinations, thereof. Various amounts of non-nicotine vapor former may be used. For example, in some example embodiments, the at least one non-nicotine vapor former is included in an amount ranging from about 20% by weight based on the weight of the non-nicotine pre-vapor formulation to about 90% by weight based on the weight of the non-nicotine pre-vapor formulation (e.g., the non-nicotine vapor former is in the range of about 50% to about 80%, or about 55% to 75%, or about 60% to 70%), etc. As another example, in at least one example embodiment, the non-nicotine pre-vapor formulation includes a weight ratio of the diol to glycerin that ranges from about 1:4 to 4:1, where the diol is propylene glycol, or 1,3-propanediol, or combinations thereof. In at least one example embodiment, this ratio is about 3:2. Other amounts or ranges may be used.

In at least one example embodiment, the non-nicotine pre-vapor formulation includes water. Various amounts of water may be used. For example, in some example embodiments, water may be included in an amount ranging from about 5% by weight based on the weight of the non-nicotine pre-vapor formulation to about 40% by weight based on the weight of the non-nicotine pre-vapor formulation, or in an amount ranging from about 10% by weight based on the weight of the non-nicotine pre-vapor formulation to about 15% by weight based on the weight of the non-nicotine pre-vapor formulation. Other amounts or percentages may be used. For example, in at least one example embodiment, the remaining portion of the non-nicotine pre-vapor formulation that is not water (and not the non-nicotine compound and/or flavorants), is the non-nicotine vapor former (described above), where the non-nicotine vapor former is between 30% by weight and 70% by weight propylene glycol, and the balance of the non-nicotine vapor former is glycerin. Other amounts or percentages may be used.

In at least one example embodiment, the non-nicotine pre-vapor formulation includes at least one flavorant in an amount ranging from about 0.2% to about 15% by weight (for instance, the flavorant may be in the range of about 1% to 12%, or about 2% to 10%, or about 5% to 8%). In at least one example embodiment, the at least one flavorant includes volatile *cannabis* flavor compounds (flavonoids). In at least one example embodiment, the at least one flavorant includes flavor compounds instead of, or in addition to, the *cannabis* flavor compounds. In at least one example embodiment, the at least one flavorant may be at least one of a natural flavorant, an artificial flavorant, or a combination of a natural flavorant and an artificial flavorant. For instance, the at least one flavorant may include menthol, wintergreen, peppermint, cinnamon, clove, combinations thereof, and/or extracts thereof. In addition, flavorants may be included to provide herb flavors, fruit flavors, nut flavors, liquor flavors, roasted flavors, minty flavors, savory flavors, combinations thereof, and any other desired flavors.

In at least one example embodiment, the non-nicotine compound may be a medicinal plant, or a naturally occurring constituent of the plant that has a medically-accepted therapeutic effect. The medicinal plant may be a *cannabis* plant, and the constituent may be at least one *cannabis*-derived constituent. Cannabinoids (phytocannabinoids) are an example of a *cannabis*-derived constituent, and cannabinoids interact with receptors in the body to produce a wide range of effects. As a result, cannabinoids have been used for a variety of medicinal purposes. *Cannabis*-derived materials may include the leaf and/or flower material from one or more species of *cannabis* plants, or extracts from the one or more species of *cannabis* plants. In at least one example embodiment, the one or more species of *cannabis* plants includes *Cannabis sativa*, *Cannabis indica*, and *Cannabis ruderalis*. In some example embodiments, the non-nicotine pre-vapor formulation includes a mixture of *cannabis* and/or *cannabis*-derived constituents that are, or are derived from, 60-80% 70%) *Cannabis sativa* and 20-40% (e.g., 30%) *Cannabis indica*.

Examples of *cannabis*-derived cannabinoids include tetrahydrocannabinolic acid (THCA), tetrahydrocannabinol (THC), cannabidiolic acid (CBDA), cannabidiol (CBD), cannabinol (CBN), cannabicyclol (CBL), cannabichromene (CBC), and cannabigerol (CBG). Tetrahydrocannabinolic acid (THCA) is a precursor of tetrahydrocannabinol (THC), while cannabidiolic acid (CBDA) is precursor of cannabidiol (CBD). Tetrahydrocannabinolic acid (THCA) and cannabidiolic acid (CBDA) may be converted to tetrahydrocannabinol (THC) and cannabidiol (CBD), respectively, via heating. In at least one example embodiment, heat from the heater 60 may cause decarboxylation to convert tetrahydrocannabinolic acid (THCA) in the non-nicotine pre-vapor formulation to tetrahydrocannabinol (THC), and/or to convert cannabidiolic acid (CBDA) in the non-nicotine pre-vapor formulation to cannabidiol (CBD).

In instances where both tetrahydrocannabinolic acid (THCA) and tetrahydrocannabinol (THC) are present in the non-nicotine pre-vapor formulation, the decarboxylation and resulting conversion will cause decrease in tetrahydrocannabinolic acid (THCA) and an increase in tetrahydrocannabinol (THC). At least 50% (e.g., at least 87%) of the tetrahydrocannabinolic acid (THCA) may be converted to tetrahydrocannabinol (THC), via the decarboxylation process, during the heating of the non-nicotine pre-vapor formulation for purposes of vaporization. Similarly, in instances where both cannabidiolic acid (CBDA) and cannabidiol (CBD) are present in the non-nicotine pre-vapor formulation, the decarboxylation and resulting conversion will cause a decrease in cannabidiolic acid (CBDA) and an increase in cannabidiol (CBD). At least 50% (e.g., at least 87%) of the cannabidiolic acid (CBDA) may be converted to cannabidiol (CBD), via the decarboxylation process, during the heating of the non-nicotine pre-vapor formulation for purposes of vaporization.

The non-nicotine pre-vapor formulation may contain the non-nicotine compound that provides the medically-accepted therapeutic effect (e.g., treatment of pain, nausea, epilepsy, psychiatric disorders). Details on methods of treatment may be found in U.S. application Ser. No. 15/845,501, filed Dec. 18, 2017, titled "VAPORIZING DEVICES AND METHODS FOR DELIVERING A COMPOUND USING THE SAME," the disclosure of which is incorporated herein in its entirety by reference.

Referring back to FIG. 1, in at least one example embodiment, the wick 224 may include filaments (or threads) having a capacity to draw non-nicotine pre-vapor formulation from the reservoir 220. For example, the wick 224 may be a bundle of glass (or ceramic) filaments, a bundle including a group of windings of glass filaments, or the like, all of which arrangements may be capable of drawing non-nicotine pre-vapor formulation via capillary action by interstitial spacing between the filaments. The filaments may be generally aligned in a direction perpendicular (transverse) to the longitudinal direction of the non-nicotine e-vaping device 10. In at least one example embodiment, the wick 224 may include one to eight filament strands, each strand comprising a plurality of glass filaments twisted together. The end portions of the wick 224 may be flexible and foldable into the confines of the reservoir 220. The filaments may have a cross-section that is generally cross-shaped, clover-shaped, Y-shaped, or in any other suitable shape.

In at least one example embodiment, the wick 224 may include any suitable material or combination of materials. Examples of suitable materials may be, but not limited to, glass, ceramic- or graphite-based materials. The wick 224 may have any suitable capillary drawing action to accommodate non-nicotine pre-vapor formulations having different physical properties such as density, viscosity, surface tension and vapor pressure. The wick 224 may be conductive or non-conductive.

In at least one example embodiment, the heater 240 may include a coil of wire (a heater coil), which at least partially surrounds the wick 224. The wire used to form the coil of wire may be metal. The heater 240 may extend fully or partially along the length of the wick 224. The heater 240 may further extend fully or partially around the circumference of the wick 224. In some example embodiments, the heater 240 may or may not be in contact (or direct contact) with the wick 224.

In at least some other example embodiments, the heater 240 may be in the form of a planar body, a ceramic body, a single wire, a mesh, a cage of resistive wire or any other suitable form. More generally, the heater 240 may be any heater that is configured to vaporize a non-nicotine pre-vapor formulation.

In at least one example embodiment, the heater 240 may heat non-nicotine pre-vapor formulation in the wick 224 by thermal conduction. Alternatively, heat from the heater 240 may be conducted to the non-nicotine pre-vapor formulation by means of a heat conductive element or the heater 240 may transfer heat to the incoming ambient air that is drawn through the non-nicotine e-vaping device 10 during non-nicotine vaping, which in turn heats the non-nicotine pre-vapor formulation by convection.

In at least one example embodiment, the heater 240 may be formed of any suitable electrically resistive materials. Examples of suitable electrically resistive materials may include, but are not limited to, copper, titanium, zirconium, tantalum and metals from the platinum group. Examples of suitable metal alloys include, but are not limited to, stainless steel, nickel, cobalt, chromium, aluminum-titanium-zirconium, hafnium, niobium, molybdenum, tantalum, tungsten, tin, gallium, manganese and iron-containing alloys, and super-alloys based on nickel, iron, cobalt, stainless steel. For example, the heater 240 may be formed of nickel aluminide, a material with a layer of alumina on the surface, iron aluminide and other composite materials, the electrically resistive material may optionally be embedded in, encapsulated or coated with an insulating material or vice-versa, depending on the kinetics of energy transfer and the external physicochemical properties required. The heater 240 may include at least one material selected from the group consisting of stainless steel, copper, copper alloys, nickel-chromium alloys, super alloys and combinations thereof. In at least one example embodiment, the heater 240 may be formed of nickel-chromium alloys or iron-chromium alloys. In another example embodiment, the heater 240 may be a ceramic heater having an electrically resistive layer on an outside surface thereof.

According to at least one example embodiment, the first outer housing 104 and the second outer housing 204 may have a generally cylindrical cross-section. In other example embodiments, the first and second outer housings 104 and 204 may have a generally triangular, rectangular, oval, square, or polygonal cross-section. Furthermore, the first and second outer housings 104 and 204 may have the same or different cross-section shape, or the same or different size. As discussed herein, the first and second outer housings 104 and 204 may also be referred to as outer or main housings.

Although example embodiments may be described in some instances with regard to the first section 100 coupled to the second section 200, example embodiments should not be limited to these examples.

The first section 100 may be a reusable section of the non-nicotine e-vaping device 10, wherein the reusable section may be capable of being recharged by an external charging device. Alternatively, the first section 100 may be disposable. In this example, the first section 100 may be used until the energy from the power supply 110 is depleted (e.g., the energy falls below a threshold level).

The power supply 110 may be a Lithium-ion battery, or a variant of a Lithium-ion battery, such as a Lithium-ion polymer battery. The power supply 110 may either be disposable or rechargeable.

The air inlet 160 may be one or more holes bored into the first outer housing 104. The air inlet 160 allows for puff detection by the sensor 134 resulting from changes in pressure when air is drawn in through air inlets 160.

Although one hole is shown in FIG. 1 for the air inlet 160, example embodiments should not be limited to this example. Rather, the first outer housing 104 may include any number of holes or air inlets 160. In at least one example embodiment, the air inlet 160 may be sized and configured such that the non-nicotine e-vaping device 10 has a resistance-to-draw (RTD) in the range of from about 60 mm $H_2O$ to about 150 mm $H_2O$.

The air outlet 250 may be one or more holes bored into the second outer housing 204 or a separate mouthpiece at an end of housing 204. Although one hole is shown in FIG. 1 for the air outlet 250, example embodiments should not be limited to this example. Rather, the second outer housing 204 may include any number of holes or air outlets 250. In at least one example embodiment, the air outlet 250 may be sized and configured such that the non-nicotine e-vaping device 10 has a resistance-to-draw (RTD) in the range of from about 60 mm $H_2O$ to about 150 mm $H_2O$.

A continuous air passage may exist between the air inlet 160 and air outlet 250 such that air is drawn in the air inlet 160 past the heater 240 and out the air outlet 250.

Figure 2:
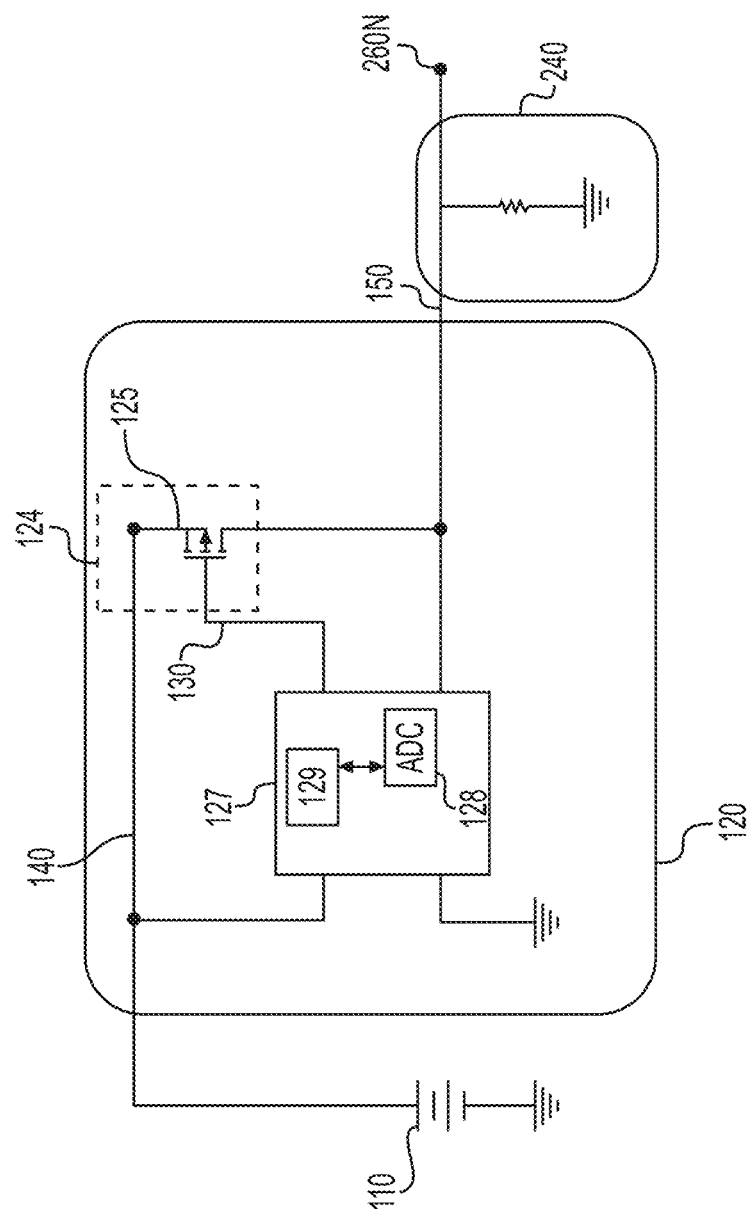
FIG. 2 is a diagram of an electrical system of the non-nicotine e-vaping device and the heater according to at least one example embodiment.

FIG. 2 is a diagram of an electrical system of the non-nicotine e-vaping device 10 according to at least one example embodiment. In the example embodiment of FIG. 2, the power circuit 124 includes a transistor 125, where an output signal from integrated circuit 127 is input to the gate of the transistor 125 via the control wire 130. A source of the transistor 125 may be connected to a rail 140. The rail 140 being connected to the power supply 110, and the voltage applied to the rail being the voltage of the power supply 110. A drain of the transistor 125 may be connected to the power wire 150. In this configuration an output signal from the integrated circuit 127 may switch the gate of the transistor 125 ON and allow a current from the power supply 110 to pass through the power circuit 124. The power circuit 124 should not be limited to this example and may include other electrical circuitry elements such as transistors, resistors, capacitors, inductors, combinations thereof, sub-combinations thereof, or the like. For example, FIG. 12 contains an alternative embodiment for the power circuit 124.

The integrated circuit 127 may include, among other things, a controller 129. The controller 129 may include processing circuitry such as hardware including logic circuits; a hardware/software combination such as a processor executing software; or a combination thereof. For example, the processing circuitry more specifically may include, but is not limited to, a central processing unit (CPU), an arithmetic logic unit (ALU), a digital signal processor, a microcomputer, a field programmable gate array (FPGA), a System-on-Chip (SoC), a programmable logic unit, a microprocessor, application-specific integrated circuit (ASIC), etc.

In another example embodiment, the integrated circuit 127 may be connected to a manually operable switch (not shown) for an adult vaper to activate the heater 240.

Still referring to FIG. 2, the integrated circuit 127 may further include an analog to digital converter (ADC) 128. The ADC 128 may be an oscillator-based converter. As will be described in greater detail below, the ADC 128 may be connected to the power wire 150 and configured to determine when the current through the power wire 150 changes beyond a certain threshold. For example, integrated circuit 127 (or controller 129) via the ADC 128 may detect a first bit value (e.g., '1') in response to determining that the current of the PWM signal changes by more than a threshold value during a pulse of the PWM signal, and detect a second bit value (e.g., '0') in response to determining that the current of the PWM signal does not change by more than the threshold value during a pulse of the PWM signal. The first bit value and second bit values of '1' and '0', respectively, are used only as examples. The first and second bit values may be reversed in some example embodiments. The ADC 128 may output a signal based on the detected current through the power wire 150. The integrated circuit 127 may determine what data has been sent based on the signal output from the ADC 128. The integrated circuit 127 may be configured to receive information from the memory module 210 only over the power wire 150. Thus, no additional electrical connections are required for data transmission between controller 212 and integrated circuit 127.

The integrated circuit 127 may determine the threshold value based on a load of the power circuit 124. For example, during an initiation phase, a bit series of "010101 . . . " may be sent by changing the load of the memory module 210 during a series of pulses of the PWM signal. The integrated circuit 127 may measure the current of data bit "0" and data bit "1" and determine the threshold for further transmissions.

In at least one example embodiment, the integrated circuit 127 may include a time-period limiter to limit the time period during which the PWM signal is continuously supplied to the heater 240. The time period may be set or pre-set depending on the amount of non-nicotine pre-vapor formulation to be vaporized. In one example, the time period for continuous application of the PWM signal to the heater 240 may be limited such that the heater 240 heats a portion of the wick 224 for less than about 10 seconds. In another example, the time period for continuous application of the PWM signal to the heater 240 may be limited such that the heater 240 heats a portion of the wick 224 for about 5 seconds.

Operation of the non-nicotine e-vaping device 10 to generate a non-nicotine vapor when the first section 100 is coupled to the second section 200 will now be described with regard to FIGS. 1 and 2.

Referring to FIG. 1, air is drawn primarily into the first section 100 through the air inlet 160 in response to application of negative pressure to the air outlet 250.

If the sensor 134 detects air flow through the first section 100 above a threshold, the sensor 134 transmits a signal to the integrated circuit 127. In response to the signal from the sensor 134, the integrated circuit 127 controls the power circuit 124 to initiate supply of the PWM signal to the heater 240, such that the heater 240 heats non-nicotine pre-vapor formulation on the wick 224 to generate a non-nicotine vapor.

The air drawn through the air inlet 160 enters the first outer housing 104, passes over the heater 240, and then flows through the air outlet 250.

The air flowing over the heater 240 combines and/or mixes with the non-nicotine vapor generated by the heater 240, and the air-vapor mixture passes through the air outlet 250.

In the example embodiment shown in FIG. 2, the PWM signal may be generated by the integrated circuit 127 by intermittently applying a voltage to the gate of the transistor in the power circuit 124.

Figure 3:
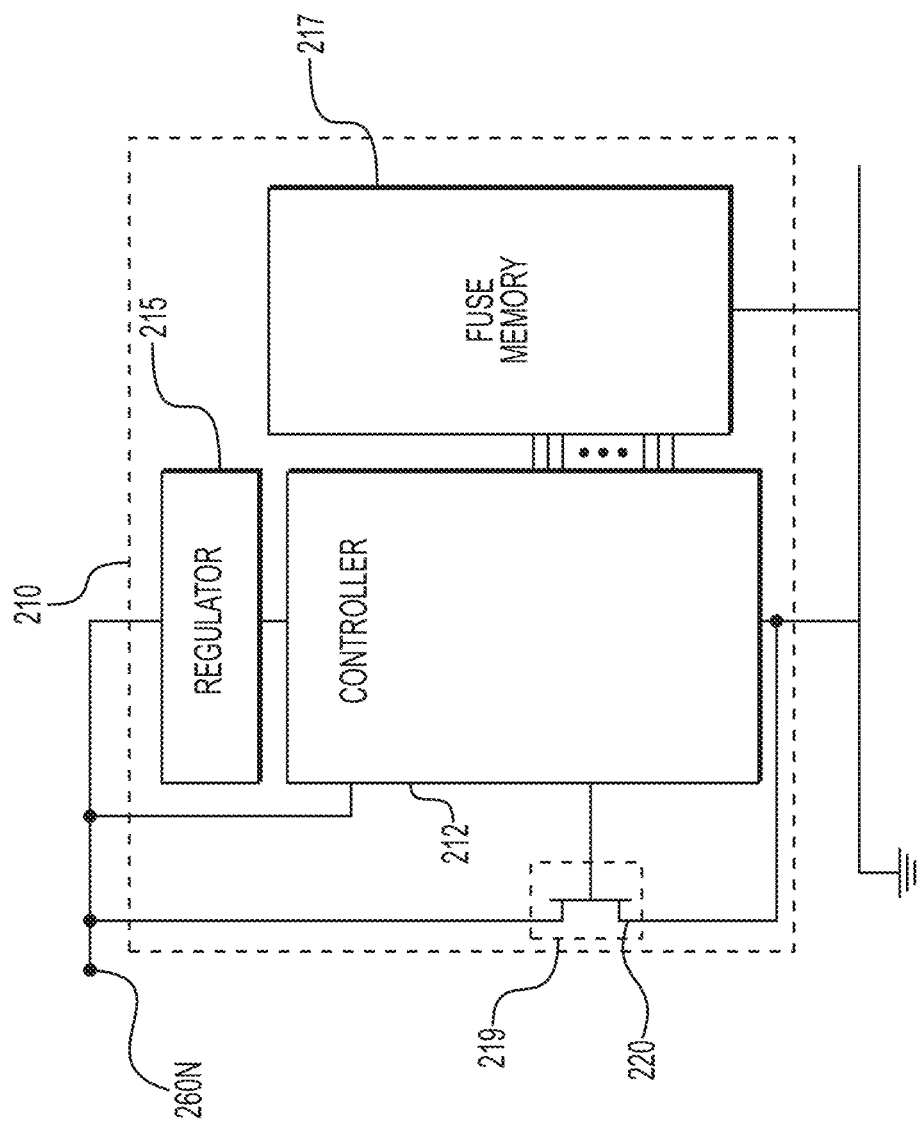
FIG. 3 is a diagram of a memory module according to at least one example embodiment.

FIG. 3 is a diagram of the memory module 210 according to at least one example embodiment. FIGS. 2 and 3 are connected at node 260N.

The memory module 210 may be connected directly or indirectly to the power wire 150. The memory module 210 may include a regulator 215, a controller (or memory controller) 212, a fuse memory 217, and an additional load 219.

The regulator 215 may be connected directly or indirectly to the power wire 150 and may be configured to charge a decoupling capacitor (not shown) within the regulator 215 to provide power to the controller 212. In some example embodiments, the regulator 215 may be omitted. The controller 212 may also be directly or indirectly connected to the power wire 150. The controller 212 may be configured to receive data transmitted over the power wire 150 (via node 260N) based on the PWM signal. Example methods and protocols by which the controller 212 may receive data based on the PWM signal will be described below with regard to FIGS. 7-11. The controller 212 may operate using power received directly from the PWM signal and may operate using power received from the regulator 215 in the gaps between the pulses in the PWM signal. The memory module 210 may be configured to receive power only from the PWM signal over the power wire 150.

The controller 212 may include processing circuitry such as hardware including logic circuits; a hardware/software combination such as a processor executing software; or a combination thereof. For example, the processing circuitry more specifically may include, but is not limited to, a central processing unit (CPU), an arithmetic logic unit (ALU), a digital signal processor, a microcomputer, a field programmable gate array (FPGA), a System-on-Chip (SoC), a programmable logic unit, a microprocessor, application-specific integrated circuit (ASIC), etc.

As described in more detail later with regard to FIGS. 7-11, the controller 212 may transmit data over the power wire 150 by selectively connecting and disconnecting the additional load 219 to and from the power wire 150 (e.g., connecting the additional load 219 to the power wire 150 during a portion of a pulse of the PWM signal to indicate a first bit value ('1'), and not connecting the additional load 219 to the power wire 150 during a pulse of the PWM signal to indicate a second bit value ('0')).

The controller 212 may also record received information in the fuse memory 217 by applying a voltage across fuses included in the fuse memory 217. The fuse memory 217 may include an array of fuses. Each fuse in the array of fuses may be opened by applying a voltage above a set voltage across the fuse. For example, the fuses may be have the set voltage for opening the fuse of about 2 volts. The controller 212 may be configured to apply a voltage above the set voltage (in this example, above 2 volts) across fuses to open fuses in the fuse array. In one example, the fuse memory 217 may include an array of 1024 fuses with the first 1016 fuses being dedicated to recording information related to an amount of non-nicotine pre-vapor formulation left in the reservoir 220, and the remaining 8 fuses dedicated to storing other information, such as a product identifier, serial number, or the like.

The additional load 219 may be connected between the power wire 150 and ground. The additional load 219 may be a transistor 220 with the gate of the transistor 220 connected to the controller 212. In one example, the transistor 220 may be a NMOS transistor. In another example, the transistor 220 may be a PMOS transistor.

The additional load may also be implemented in other configurations. For example, the additional load 219 may include multiple transistors, resistors, capacitors, a combination thereof, or a sub-combination thereof.

Figure 4A:
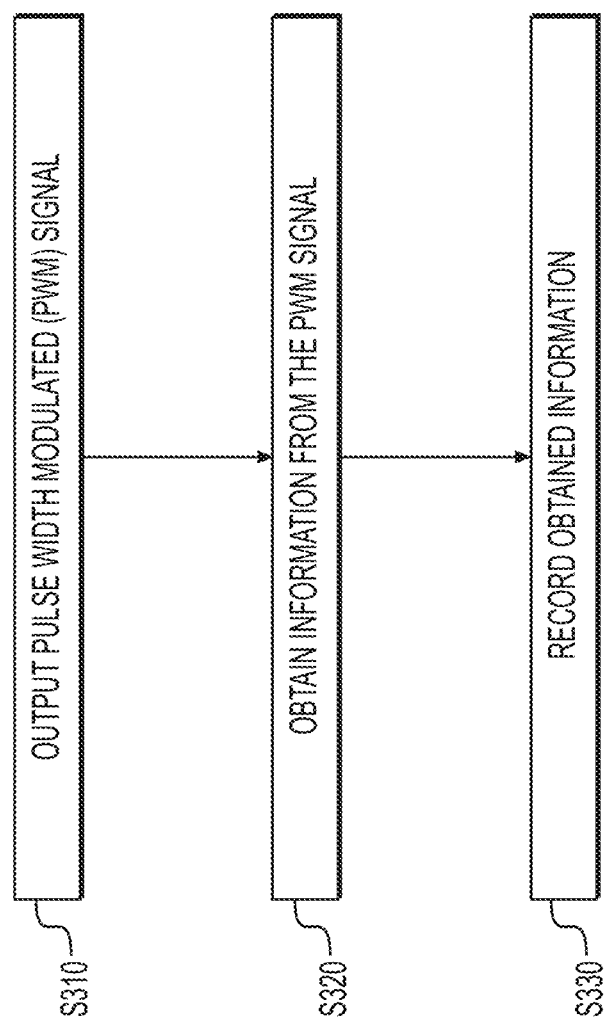
FIG. 4A is a flow diagram illustrating a method for recording information to the memory module according to at least one example embodiment.

FIG. 4A is a flow diagram illustrating a method for recording information to the memory module 210 according to at least one example embodiment. For example purposes, the method shown in FIG. 4A will be discussed with regard to the non-nicotine e-vaping device and electrical system shown in FIGS. 1-3.

At S310, the power control circuit 120 outputs the PWM signal to the controller 212 over the power wire 150 based on the battery voltage. The power control circuit 120 may output the PWM signal in response to a signal from the sensor 134. The PWM signal may be a rectangular PWM signal or may include embedded signals within the PWM signal. The PWM signal is received at the controller 212 via the power wire 150.

At S320, the controller 212 obtains information from the PWM signal. For example, the controller 212 may detect a number of pulses in the PWM signal and determine a time in which the heater 240 is operational (operating time) based on the number of detected pulses. The controller 212 may also determine information to record based on the number of detected pulses or the time in which the heater 240 is operational. As another example, the controller 212 may detect a signal embedded in the PWM signal and determine information to record based on the signal embedded in the PWM signal. Example methods and protocols for embedding signals within the PWM signal will be discussed later with regard to FIGS. 7-11.

At S330, the controller 212 records the obtained information. For example, the obtained information may be the time in which the heater 240 is operational, and the controller 212 may open one fuse in the fuse memory 217 for every second the heater 240 is operated based on the number of pulses in the PWM signal. As another example, the controller 212 may open a number of fuses based on information carried by the signal embedded in the PWM signal. For example, the embedded signal may include an indication of the number of fuses to be opened. The embedded signal may also include other commands such as a request for the memory 217 to send a signal indicating the number of fuses already opened in the portion of the fuses dedicated to the amount of non-nicotine pre-vapor formulation in the reservoir 220. Alternatively, the controller 212 may be programmed to send data indicating the number of fuses already opened if the PWM signal continues for at least a set number of pulses.

FIG. 4B is a flow diagram illustrating a method for transmitting information to the main body according to at least one example embodiment.

At S340, the controller 212 may transmit data via the power wire 150 by modifying the load of the power circuit 124 while the PWM signal is output by the power control circuit 120. Since the battery acts as a voltage source, the change in load will change the current drawn through the power wire 150. The change in load may be accomplished by connecting an additional load 219 to the power wire 150. For example, the additional load 219 may comprise a transistor 220. The transistor 220 may be turned on by the controller 212 applying a voltage to the gate of the transistor 219. The transistor 220 may be connected between the power wire 150 and ground. The current flow through the power wire 150 increases when the transistor 220 is switched on. Thus, the controller 212 may modify the load of the power circuit 124 by turning on the transistor 220. In this way, the controller 212 may communicate information by selectively modifying the load (e.g., turning the transistor 220 on and off) of the power circuit 124 during a PWM clock cycle. Thus, the controller 212 may output the information recorded in the fuse memory 217 to the power control circuit 120 via the power wire 150. Restated, the controller 212 may output the recorded information via the power wire 150 during output of the PWM signal to the heater 240 over the power wire 150 by the power control circuit 120. Example methods and protocols for transmitting or communicating information by selectively modifying the load of the power circuit 124 will be discussed later with regard to FIGS. 7-11.

At S350, the integrated circuit 127 (via the ADC 128) detects the transmitted data by measuring the current of the PWM signal in response to a change in current caused by the connection of the additional load 219 by the controller 212. That is, for example, the integrated circuit 127 senses a change in current drawn through the power wire 150 and detects the transmitted data based on the sensed change in the current drawn through the power wire 150. The data may include a final bit or bits as a checksum (e.g., including at least one parity bit or confirmation bit).

At S360, the integrated circuit 127 determines if the data was received without error. The integrated circuit 127 may determine if the data was received without error using the checksum bit or bits to check the sum of the previously received bits against the checksum. Because methods for determining whether data is received correctly using a checksum is known, further discussion is omitted.

If the integrated circuit 127 determines that the data was received without error at S360, then the integrated circuit 127 may control the power circuit 124 to transmit a receipt acknowledgement via the PWM signal at S370. The acknowledgement may be embedded in the PWM signal. Alternatively, the acknowledgement receipt may be sent by transmitting a set pulse in the PWM signal without modification. Example methods and protocols for embedding information (e.g., acknowledgment information or bit(s)) within a PWM signal will be discussed later with regard to FIGS. 7-11.

Returning to S360, if the integrated circuit 127 determines that the data was received with errors (e.g., the checksum failed), then the integrated circuit 127 may control the power circuit 124 to transmit a request to resend the data (negative acknowledgment) via the PWM signal. The request may be embedded in the PWM signal as discussed in more detail later with regard to FIGS. 7-11. Alternatively, as will be described in further detail below, the request to resend the data may be transmitted by shortening a set pulse in the PWM signal. Based on the request to resend the data (or negative acknowledgement), the memory module 210 may resend the data.

Using the same or substantially the same operations, the integrated circuit 127 may request and receive information (e.g., a product identification, serial number, a combo thereof, or the like) stored in the fuse memory 217.

The integrated circuit 127 may determine a number of LEDs among the LED array 137 to activate based on the data. For example, the data may indicate a total number of seconds the heater 240 has been active (as represented by the data stored in the fuse memory 217). The integrated circuit 127 may determine the percentage (or fraction) of the total time the heater 240 can be active before the reservoir 220 is depleted (e.g., all or substantially all the non-nicotine pre-vapor formulation stored in the reservoir 220 is vaporized, the reservoir 220 is empty, or falls below a threshold level), represented by the total number of seconds the heater 240 has been active, and activate the same percentage of the LEDs in the LED array 137. The integrated circuit 127 may know a priori or determine the total time the heater 240 can be active before the non-nicotine pre-vapor formulation stored in the reservoir 220 is depleted in several different ways. For example, the data may indicate a total number of seconds the heater 240 can be active before the non-nicotine pre-vapor formulation stored in the reservoir 220 is depleted. As another example, the integrated circuit 127 may be pre-programmed with the number of seconds the heater 240 can be active before the non-nicotine pre-vapor formulation in the reservoir 220 is depleted. As yet another example, the integrated circuit 127 may be pre-programmed with the number of seconds the heater 240 can be active for a certain product type before the reservoir 220 is depleted. In this case, the integrated circuit 127 may request the product type from the memory module 210, and determine the number of seconds based on the identified product type.

As another example, the controller 212 may determine the number of LEDs in the LED array 137 to activate based on the above mentioned percentage, and the controller 212 may send data to the integrated circuit 127 indicating the determined number of LEDs in the LED array 137. The integrated circuit 127 may activate the LEDs in the LED array 137 according to the number indicated in the data.

Figure 5:
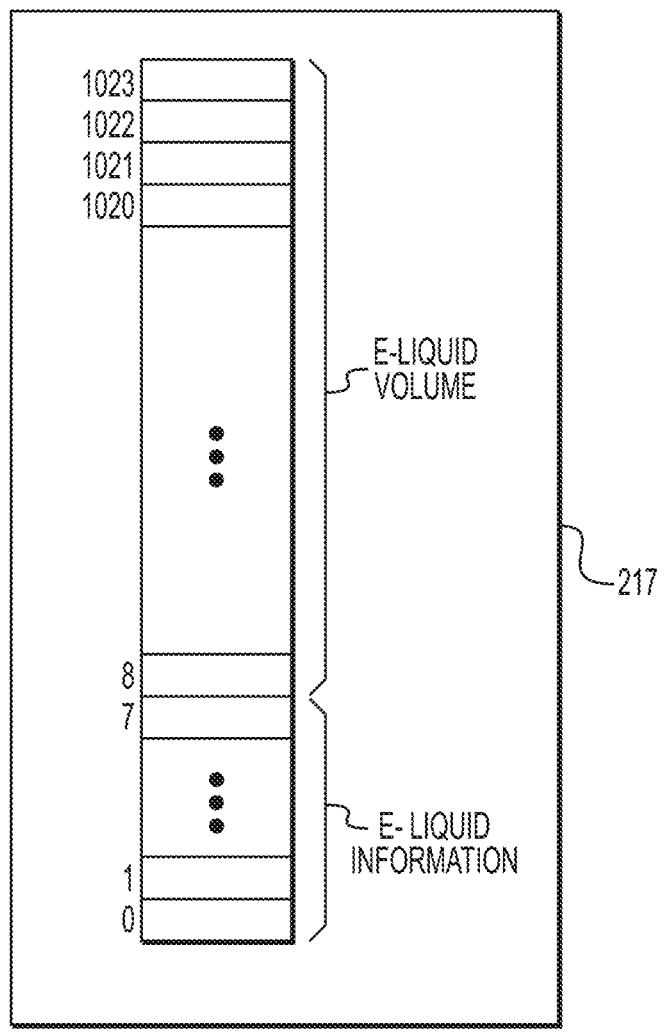
FIG. 5 is block diagram of a fuse memory according to at least one example embodiment.

FIG. 5 is block diagram of the fuse memory 217 according to at least one example embodiment.

As mentioned above, the fuse memory 217 may include an array of fuses. For example, the array of fuses may include 1024 fuses. The reservoir 220 may include sufficient non-nicotine pre-vapor formulation for the heater 240 to vaporize non-nicotine pre-vapor formulation for about 1016 seconds. A first portion of the fuse array, (e.g., 1016 fuses) may represent the total operational time of the heater 240. A second portion (e.g., 8 fuses) may store other information, such as a product identifier or serial number for the cartridge 200. The number of fuses in the section of the fuse memory 217 need not correlate one to one with the number of seconds the heater 240 is actively heating non-nicotine pre-vapor formulation to generate non-nicotine vapor before the reservoir 220 is depleted, but may correlate to any amount of time. For example, if the reservoir 220 only holds non-nicotine pre-vapor formulation sufficient for the heater 240 to operate for about 508 seconds before the reservoir 220 is depleted, then the first portion of the fuses array may still include 1016 fuses, wherein each represents one half second of the total operation time of the heater 240.

The fuse array may store other information in the second portion as well as including information representing at least one flavor of the non-nicotine pre-vapor formulation, a date, or other information related to the cartridge 200.

Figure 6:
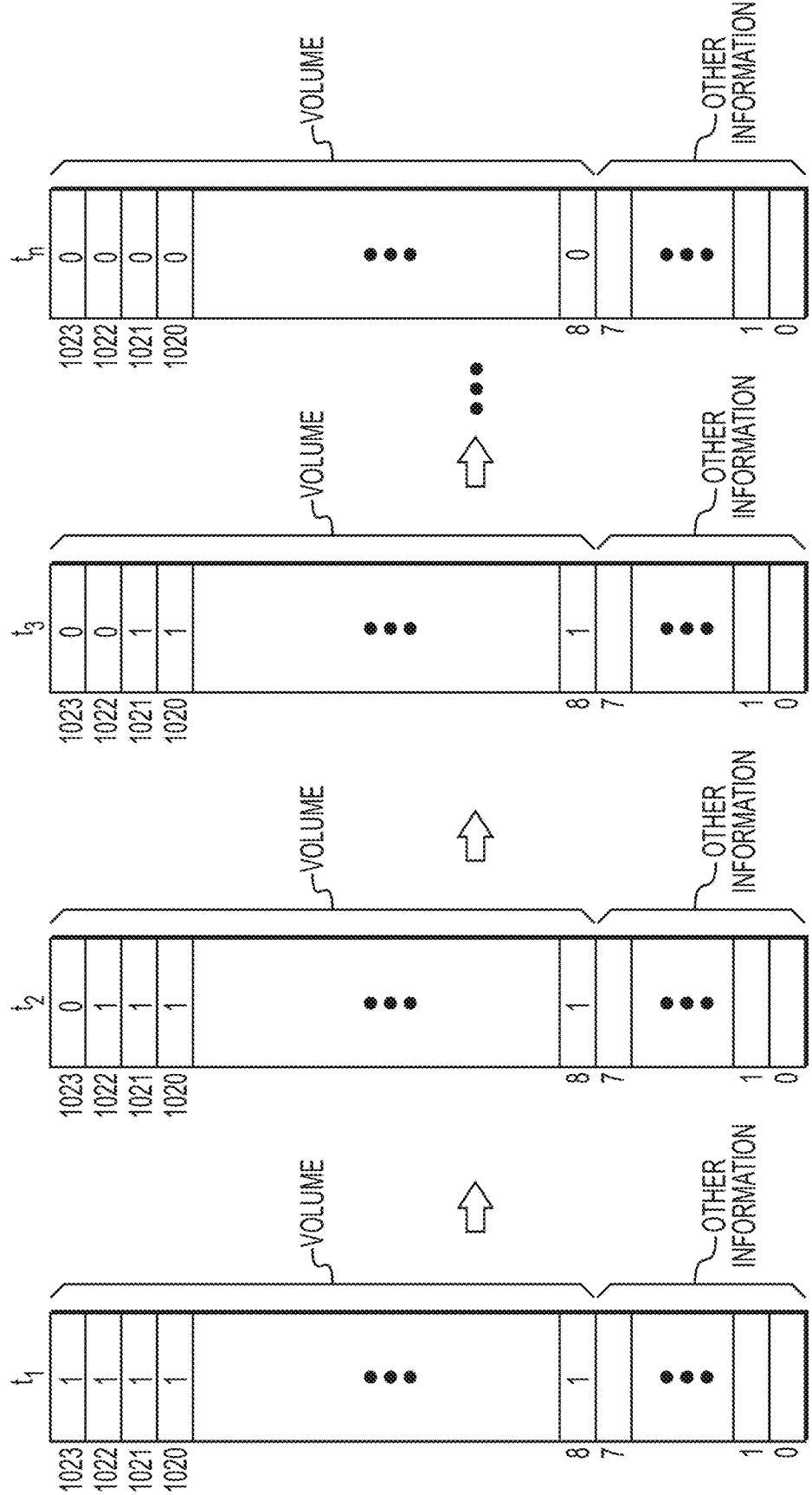
FIG. 6 is a time lapse diagram illustrating an example recording operation according to at least one example embodiment.

FIG. 6 is a time lapse diagram showing the recording of information in the fuse memory 217 according to at least one example embodiment.

FIG. 6 shows an example of how the controller 212 may apply the set voltage across one of the fuses at each time $t_i$ from $t_1$ to $t_n$. For example, if the time from each time $t_i$ to the next time $t_{i+1}$ is one second and the PWM signal has a period of 50 ms, then the controller 212 may apply the set voltage across one of the fuses after 20 pulses have been received at $t_1$. The controller 212 may then apply the set voltage across a second fuse after another 20 pulses have been received at time $t_2$. In this way, one fuse will be opened for each set of 20 pulses received by the heater 240 and the controller 212.

According to at least some example embodiments, the fuses are opened permanently and do not require a maintained voltage to hold the open or closed position. Thus, the fuse memory 217 is non-volatile. Accordingly, even after the non-nicotine e-vaping device 10 has been turned off and back on again, the controller 212 may continue recording information about the total operating time of the heater 240 by continuing to open one fuse at each time t. The ability of the fuses to hold an open or closed state is also not significantly affected by the heat generated by the heater 240. Accordingly, the above described fuse memory 217 is able to maintain information without a constant voltage and without being significantly affected by the heat produced by the heater 240. Fuse memories are also generally less costly than heat resistant Electrically Erasable Programmable Read-Only Memory (EEPROM).

The controller 212 may be configured to determine which fuses have not been opened in order to know which fuse to open next. The controller 212 may also determine how many fuses are already open in the portion of the fuses dedicated to the amount of non-nicotine pre-vapor formulation in the reservoir 220 in order to respond to the request for the memory module 210 to send a signal indicating the amount of non-nicotine pre-vapor formulation remaining in the reservoir 220.

Figure 7:
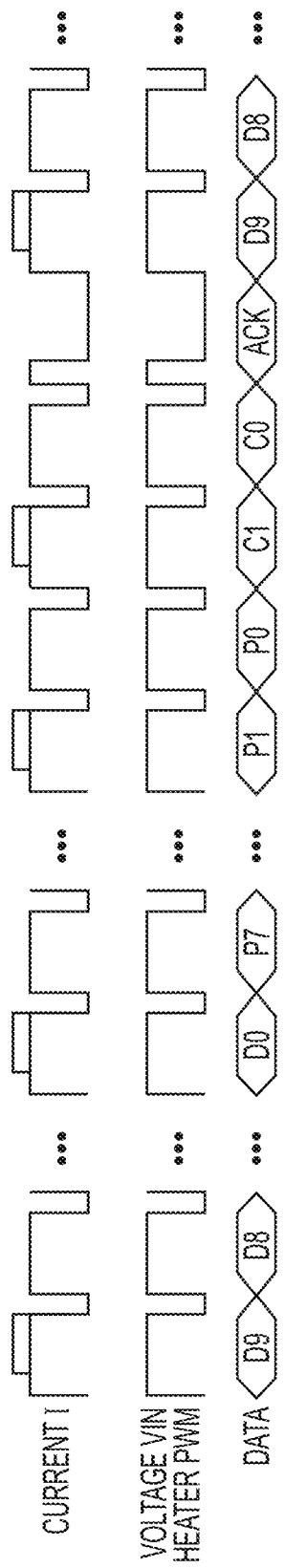
FIG. 7 is an example pulse width modulated signal according to at least one example embodiment.
Figure 8:
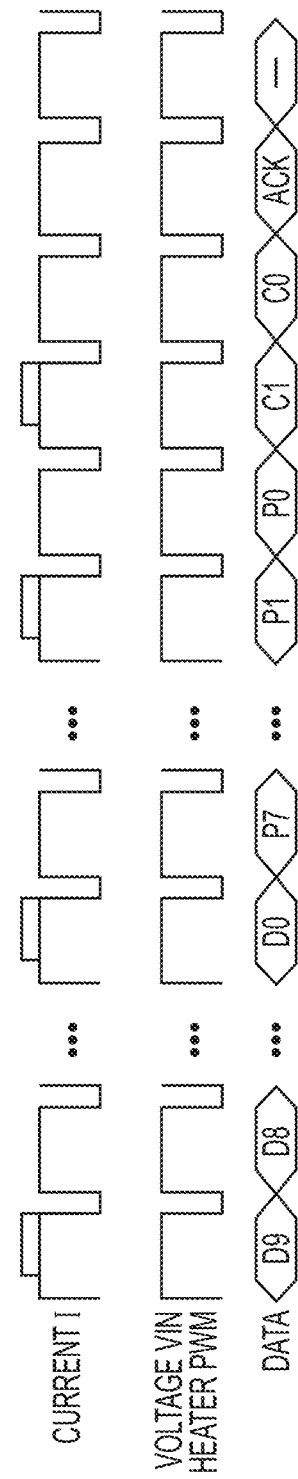
FIG. 8 is another example pulse width modulated signal according to at least one example embodiment.

FIG. 7 is an example PWM signal according to at least one example embodiment. FIG. 8 is another example PWM signal according to at least one example embodiment In FIGS. 7 and 8, the power control circuit 120 and memory module 210 may communicate according to a first protocol. The upper graph shows current through the power wire 150, and the middle graph shows the voltage of the power wire 150. The third graph shows the PWM clock cycle.

In the first protocol, the PWM signal may not include any embedded signals from the power control circuit 120.

The memory module 210 may count the number of pulses received in the PWM signal in order to determine when to open a fuse of the fuse memory 217.

The controller 212 may transmit data after scanning the data stored in the fuse memory 217. The scan of the fuse memory 217 may take about 10 PWM clock cycles.

After the scan of the fuse memory 217, the controller 212 sends formulation data indicating the number of fuses in the first portion of the fuse memory 217 which are still open; D9-D0: non-nicotine pre-vapor formulation remaining in the reservoir 220.

After the formulation data portion, the controller 212 sends the product identification or serial number stored in the second portion of the fuse memory 217; P7-P0: product identification or serial number.

After the product identification or serial number, the controller 212 transmits two check sum or parity bits; C1-C0: checksum.

If all of the information is correctly received by the power control circuit 120, then the integrated circuit 127 controls the power circuit 124 to transmit a full PWM pulse in the acknowledge (ACK) PWM clock cycle as shown in FIG. 8. If all of the information is not correctly received by the power control circuit 120, then the integrated circuit 127 controls the power circuit 124 to transmit a short PWM pulse (negative acknowledgment) in the acknowledge (ACK) PWM clock cycle as shown in FIG. 7. The short PWM pulse may have a length shorter than a previous pulse of the PWM signal (e.g., be less than half of the PWM clock cycle).

In FIG. 7, the transmitted data (including the data portion, the product identification or serial number, the checksum, combinations thereof or sub-combinations thereof) is resent in response to the short pulse in the ACK PWM clock cycle.

As described above, the controller 212 may connect an additional load 219 to increase a current through the power wire 150 in order to transmit the data. For example, in FIG. 7, the current graph for D9, D0, P1, C1 indicates data '1' is sent, whereas the current graph for D8, P7, P0, C0 indicates bit '0' is sent. The controller 212 is configured to output the data by connecting the additional load 219 to the power wire 150 during a portion of a pulse of the PWM signal to indicate a first bit value ('1'), and not connecting the additional load 219 to the power wire 150 during a pulse of the PWM signal to indicate a second bit value ('0').

Figure 9:
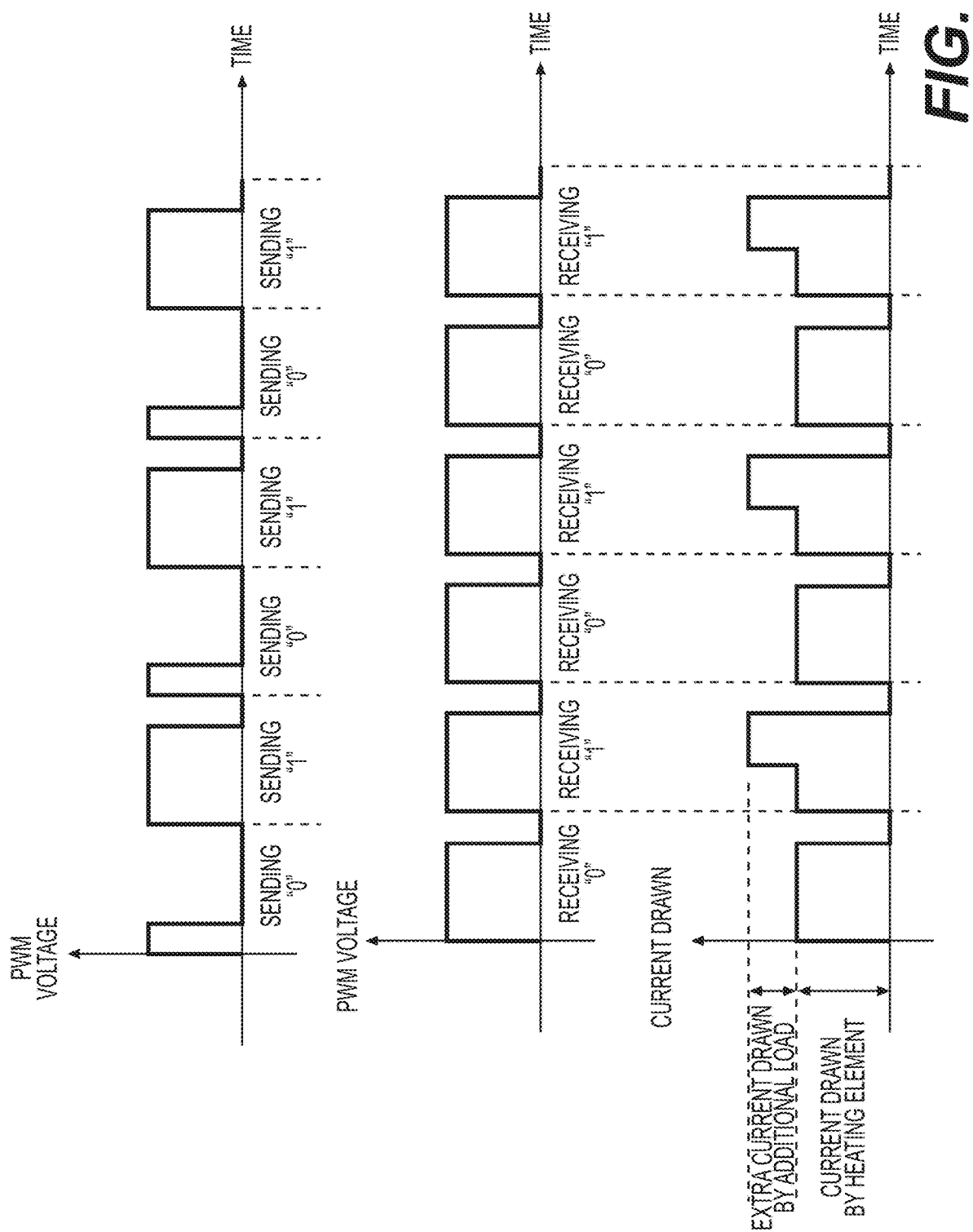
FIG. 9 is another example pulse width modulated signal according to at least one example embodiment.

FIG. 9 is another example PWM signal according to at least one example embodiment. In FIG. 9, the power control circuit 120 and memory module 210 may communicate according to a second protocol. The hardware used for communicating using the second protocol may be the same or substantially the same as the hardware used to communicate using the first protocol.

In the second protocol, the power control circuit 120 may communicate with the memory module 210 by modifying the width of the pulses in the PWM signal. For example, in the first mode, the power control circuit 120 may modify a pulse to have a width greater than 50% of the PWM clock cycle to indicate a '1.' In the second mode, the power control circuit 120 may modify a pulse to have a width less than 50% of the PWM clock cycle to indicate a '0.' The memory module 210 (more specifically the controller 212) may be configured to detect a width of a single pulse in the PWM signal and record information based on the width of the pulse. Further, the memory module 210 may be configured to detect a width of each of the pulses in the PWM signal and record information based on the widths of the pulses.

In the second protocol, the power control circuit 120 and memory module 210 may alternate which device communicates over the power wire 150. For example, the power control circuit 120 may communicate ten bits in a first ten PWM clock cycles and the memory module 210 may communicate ten bits in a second ten PWM clock cycles. In the second protocol, the memory module 210 may communicate in the same or substantially the same manner described above with relation to FIG. 4B by selectively connecting a load 219 during a PWM clock cycle.

As an alternative, both the power control circuit 120 and memory module 210 may send information in the same PWM cycle using a combination of the methods described with regard to FIGS. 7-9. In one example, the length of the pulse may indicate information being sent from the power control circuit 120 and the current through the power wire 150 may indicate information being sent by the memory module 210.

In FIG. 9, the first graph shows data being sent by the power control circuit 120 by modifying the length of the pulses in the PWM signal. The second and third graphs show the voltage and current of the power wire 150 when the memory module 210 communicates data by connecting/disconnecting the additional load 219.

Figure 10:
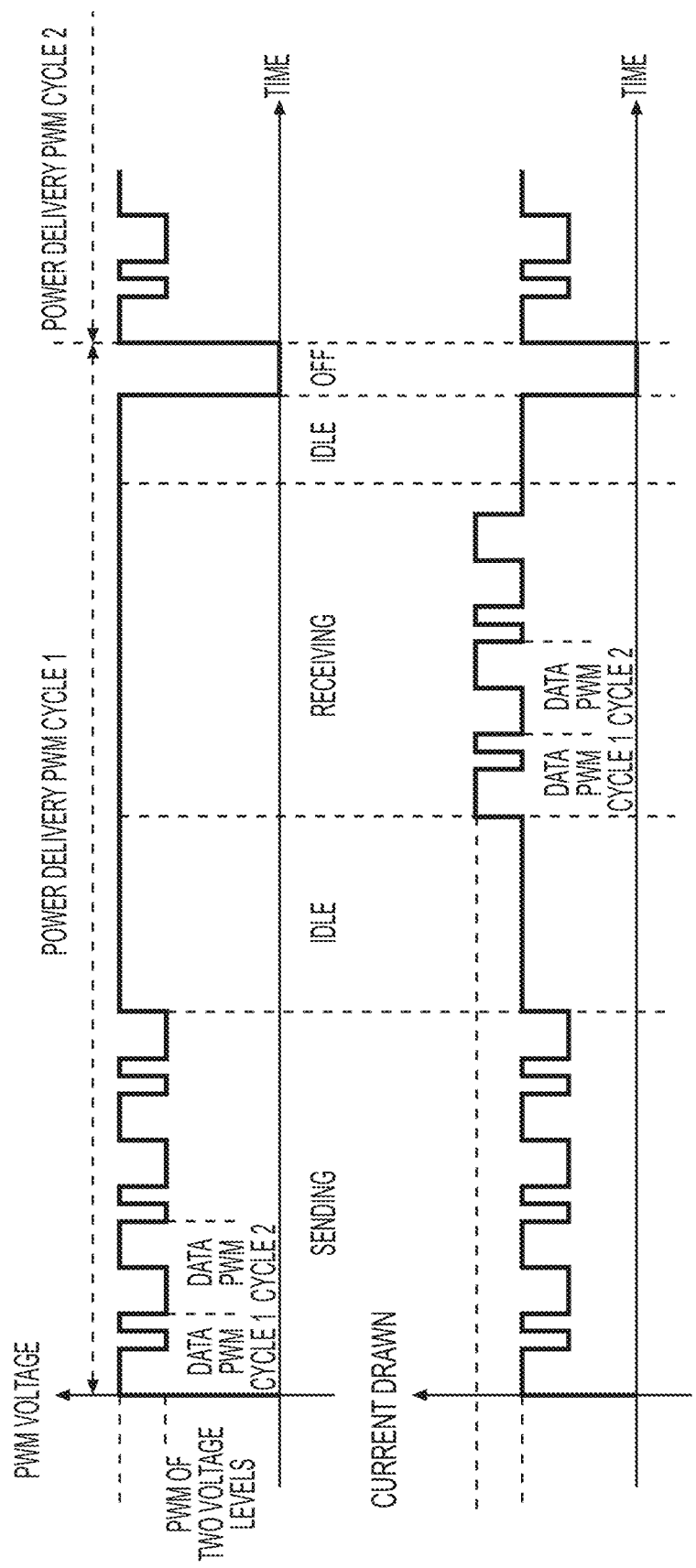
FIG. 10 is another example pulse width modulated signal according to at least one example embodiment.

FIG. 10 is another example PWM signal according to at least one example embodiment. In FIG. 10, the power control circuit 120 and memory module 210 may communicate according to a third protocol. In the third protocol, each PWM clock cycle may be divided into four sections; sending, idle, receiving, and off.

In the sending section, the power control circuit 120 may modulate the voltage of the PWM signal in order to transfer data. Several bits of data may be sent during the sending section of each pulse of the PWM signal. The sending section may include several data PWM cycles wherein a single bit may be sent. In one example, a shorter pulse of lower voltage may indicate a '1' and a longer pulse of lower voltage may indicate a '0.' For example, as shown in FIG. 10, the shorter pulse of lower voltage in cycle 1 may indicate a '1' and the longer pulse in cycle 2 may indicate a '0.'

In the idle section and receiving section of the PWM clock cycle, the voltage may be at the higher voltage of the two voltage levels. In the receiving section, the memory module 210 may communicate several data bits by selectively connecting the additional load 219 to the power wire 150 in order to draw extra current through the power wire 150. A shorter pulse of lower current, as shown in data PWM cycle 1, may indicate a '1' and a longer pulse of lower current, as shown in data PWM cycle 2, may indicate a '0.'

In the off section, the PWM signal may be at zero volts and zero amps.

Figure 11:
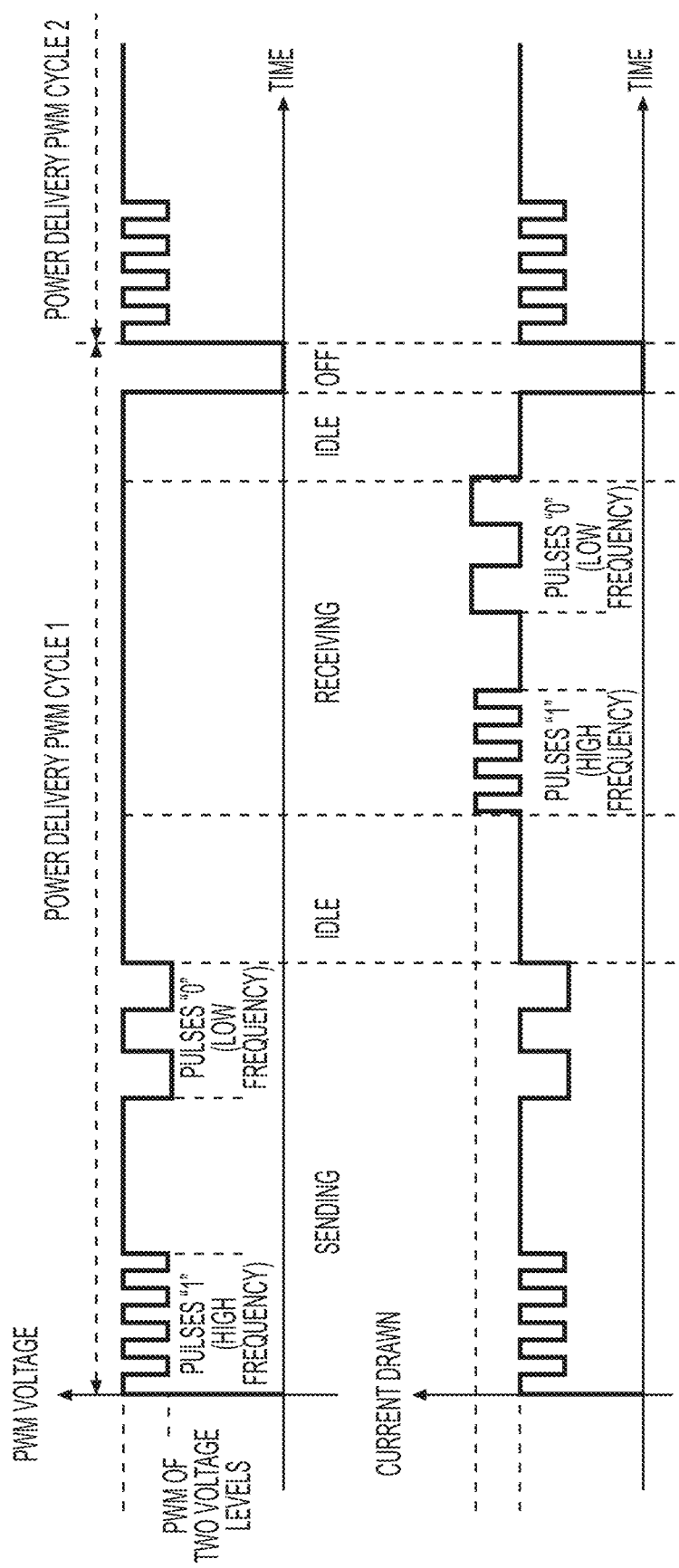
FIG. 11 is another example pulse width modulated signal according to at least one example embodiment.

FIG. 11 is another example PWM signal according to at least one example embodiment.

In FIG. 11, the power control circuit 120 and memory module 210 may communicate according to a fourth protocol. In the fourth protocol, each PWM clock cycle may be divided into four sections similarly to the third protocol.

Differently from the third protocol, the data may be sent by changing a frequency of the pulses of lower voltage (for the power control circuit 120) or higher current (for the memory module 210). In one example, group of pulses with a higher frequency may indicate a '1' and one or more low frequency pulses may indicate a '0.' The memory module 210 (more specifically the controller 212) may be configured to detect a frequency of pulses in the PWM signal and record information based on the frequency of the pulses.

Figure 12:
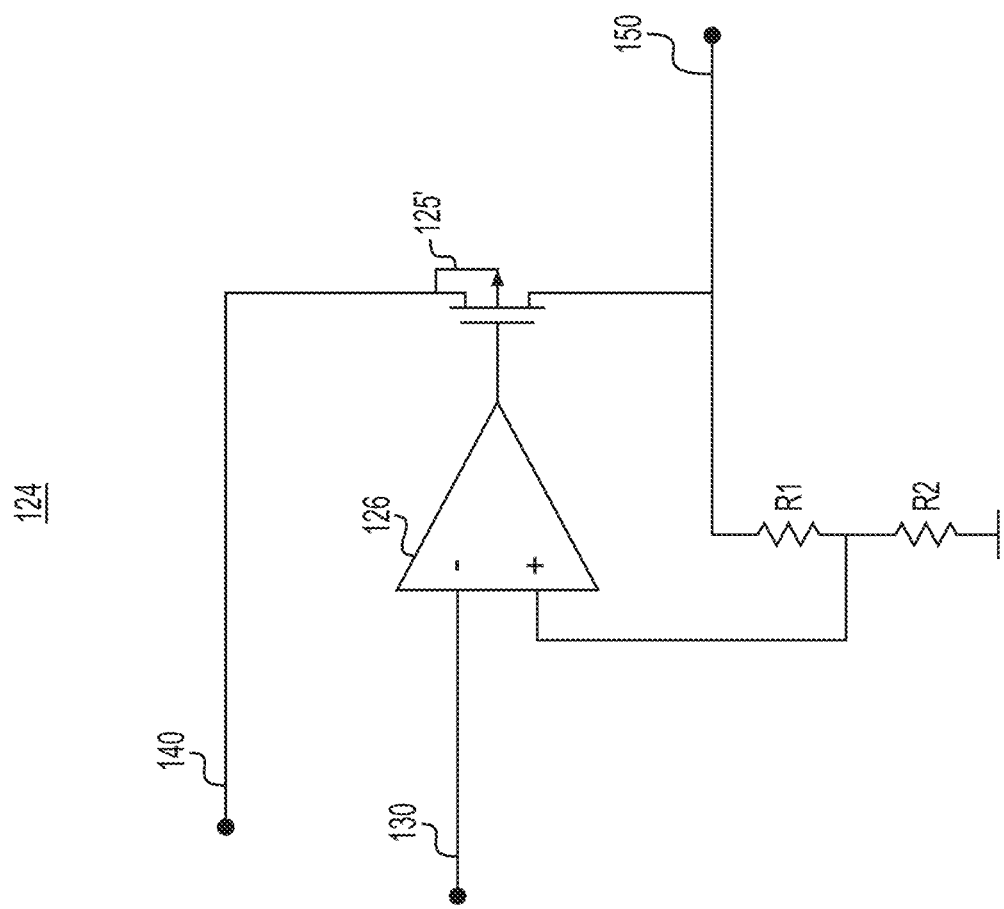
FIG. 12 is an example power circuit according to at least one example embodiment.

FIG. 12 is an example power circuit 124 according to at least one example embodiment. The power circuit 124 may include an operational amplifier 126, transistor 125', and resistors R1 and R2 arranged as a voltage dividing circuit. The operational amplifier 126 may receive the output signal from the integrated circuit 127 at a negative input terminal of the operational amplifier 126. The negative input terminal being connected to the control wire 130. The output of the operational amplifier 126 may be input to the gate of the transistor 125'. The operational amplifier 126 may receive a feedback voltage at a positive input terminal of the operational amplifier 126. The feedback voltage may be a voltage at a node between the resistors R1 and R2. The transistor 125' may have the source connected to the rail 140 and the drain connected to the power wire 150. The resistor R1 may be connected between the power wire 150 and the resistor R2. The resistor R2 may be connected between the resistor R1 and ground.

In one example embodiment, the resistances of the resistors R1 and R2 may be equal. When the resistances R1 and R2 are equal, the voltage applied to the power wire 150 will be twice the voltage of the output signal from the integrated circuit 127. Accordingly, the integrated circuit may control the voltage applied to the power wire 150 to be any voltage between ground and the rail 140 voltage based on the output signal from the integrated circuit 127.

In the example of third or fourth protocols as described above, the integrated circuit 127 may control the power circuit 124 shown in FIG. 12 to apply the PWM signal having two voltage levels to the power wire 150 by outputting an output signal which alternates between two other voltage levels. The two other voltage levels may be half of the two voltage levels applied to the power wire 150, respectively, in the case where the resistances of resistors R1 and R2 are equal.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, or the like, may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various example embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

Example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

We claim:

1. A non-nicotine e-vaping device comprising:
   a heater element configured to heat a non-nicotine pre-vapor formulation, the non-nicotine pre-vapor formulation being devoid of nicotine and including at least one non-nicotine compound;
   a power control circuit coupled to the heater element through a wire, the power control circuit configured to apply a pulse width modulated power signal to the heater element through the wire, and to receive information over the wire; and
   a memory module configured to,
      detect a plurality of pulses in the pulse width modulated power signal,
      record information based on the detected plurality of pulses, and
      output the recorded information to the power control circuit via the wire.

2. The non-nicotine e-vaping device of claim 1, wherein the memory module is configured to output the recorded information via the wire during output of the pulse width modulated power signal to the heater element over the wire by the power control circuit.

3. The non-nicotine e-vaping device of claim 1, wherein the memory module is configured to,
   detect a number of pulses included in the plurality of pulses, and
   record the information based on the number of pulses.

4. The non-nicotine e-vaping device of claim 1, wherein the memory module is configured to,
   detect a width of a pulse included in the plurality of pulses, and
   record the information based on the width of the pulse included in the plurality of pulses.

5. The non-nicotine e-vaping device of claim 1, wherein the memory module is configured to,
   detect a frequency of pulses included in the plurality of pulses, and
   record the information based on the frequency of pulses included in the plurality of pulses.

6. The non-nicotine e-vaping device of claim 1, wherein the memory module includes a fuse memory having an array of fuses, and
   the memory module is configured to record the information by opening at least one fuse among the array of fuses.

7. The non-nicotine e-vaping device of claim 6, wherein the memory module is configured to record the information by opening a fuse for every set number of pulses in the pulse width modulated power signal.

8. The non-nicotine e-vaping device of claim 7, wherein the memory module is configured to store additional information representing at least one of an identifier, a flavor of the non-nicotine pre-vapor formulation, a date, or any combination thereof.

9. The non-nicotine e-vaping device of claim 1, wherein the power control circuit is configured to apply the pulse width modulated power signal in response to application of negative pressure to the non-nicotine e-vaping device.

10. The non-nicotine e-vaping device of claim 1, wherein the memory module is further configured to receive power only from the pulse width modulated power signal, and
    the power control circuit is configured to receive the information only via the wire.

11. The non-nicotine e-vaping device of claim 1, wherein the memory module is configured to output the recorded information to the power control circuit by selectively connecting a load to the wire, and
    the power control circuit is configured to receive the recorded information by detecting a change in a current passing through the wire resulting from selective connection of the load.

12. The non-nicotine e-vaping device of claim 1, wherein the memory module is configured to output the recorded information by increasing a current through the wire during at least one pulse of the pulse width modulated power signal.

13. The non-nicotine e-vaping device of claim 1, further comprising:
    a cartridge including the memory module and a reservoir, the reservoir configured to hold the non-nicotine pre-vapor formulation; wherein
    the non-nicotine pre-vapor formulation includes a non-nicotine vapor former and the at least one non-nicotine compound.

14. The non-nicotine e-vaping device of claim 1, wherein the at least one non-nicotine compound is *cannabis*, at least one *cannabis*-derived constituent, or both *cannabis* and the at least one *cannabis*-derived constituent.

\* \* \* \* \*